US006869607B1

(12) United States Patent
Buschle et al.

(10) Patent No.: US 6,869,607 B1
(45) Date of Patent: Mar. 22, 2005

(54) VACCINE FORMULATIONS

(75) Inventors: Michael Buschle, Brunn/Gebirge (AT); Max Birnstiel, Vienna (AT); Walter Schmidt, Vienna (AT)

(73) Assignee: Intercell AG, Vienna (AT)

( * ) Notice: Subject to any disclaimer, the term of this patent is extended or adjusted under 35 U.S.C. 154(b) by 0 days.

(21) Appl. No.: 09/601,171
(22) PCT Filed: Jan. 27, 1999
(86) PCT No.: PCT/EP99/00524
§ 371 (c)(1), (2), (4) Date: Jul. 28, 2000
(87) PCT Pub. No.: WO99/38528
PCT Pub. Date: Aug. 5, 1999

(30) Foreign Application Priority Data

Jan. 30, 1998  (DE) ......................................... 198 03 453

(51) Int. Cl.[7] ........................ A61K 39/00; A61K 39/38; A61K 45/00
(52) U.S. Cl. ............................... 424/184.1; 424/278.1; 424/279.1
(58) Field of Search .......................... 424/184.1, 278.1, 424/279.1

(56) References Cited

U.S. PATENT DOCUMENTS

| | | | |
|---|---|---|---|
| 4,147,772 A | * | 4/1979 | McAleer et al. |
| 4,338,335 A | * | 7/1982 | McAleer et al. |
| 4,849,358 A | * | 7/1989 | Chazono et al. |
| 5,776,468 A | * | 7/1998 | Hauser et al. |
| 6,258,362 B1 | * | 7/2001 | Loudon et al. |

FOREIGN PATENT DOCUMENTS

| | | |
|---|---|---|
| WO | WO 95/15768 | 6/1995 |
| WO | WO 97/30721 | 8/1997 |

OTHER PUBLICATIONS

Yamana et al (Japanese Journal of Cancer & Chemotherapy vol. 27 No. 10, pp 1477–1488), Sep. 2000.*
Abraham, E., "Intranasal Immunization with Bacterial Polysaccharide Containing Liposomes Enhances Antigen–Specific Pulmonary Secretory Antibody Response," *Vaccine* 10:461–468 (1992).
Allison, A.C., and Byers, N.E., "Immunological Adjuvants: Desirable Properties and Side–Effects," *Mol. Immunol.* 28:279–284 (1991).
Azuma, I., "Synthetic Immunoadjuvants: Application to Non–Specific Host Stimulation and Potentiation of Vaccine Immunogenicity," *Vaccine* 10:1000–1006 (1992).
Baker, P.J., et al., "Ability of Monophosphoryl Lipid A to Augment the Antibody Response of Young Mice," *Infect. Immun.* 56:3064–3066 (1988).

Barr, I.G., and Mitchell, G.F., "ISCOMs (Immunostimulating Complexes): The First Decade," *Immunol. Cell Biol.* 74:8–25 (1996).
Buschle, M., et al., "Transloading of Tumor Antigen–Derived Peptides Into Antigen–Presenting Cells," *Proc. Natl. Acad. Sci. USA* 94:3256–3261 (Apr. 1997).
Byars, N.E., et al., "Improvement of Hepatitis B Vaccine by the Use of a New Adjuvant," *Vaccine* 9:309–318 (1991).
Elloux, F., et al., "Minimal Structural Requirements for Adjuvant Activity of Bacterial Peptidoglycan Derivatives," *Biochem. Biophys. Res. Commun.* 59:1317–1325 (1974).
Gregoriadis, G., "Immunological Adjuvants: A Role for Liposomes," *Immunol. Today* 11:89–97 (1990).
Gupta, R.K., and Siber, G.R., "Adjuvants for Human Vaccines–Current Status, Problems and Future Prospects," *Vaccine* 13:1263–1276 (1995).
Harrington, D.G., et al., "Adjuvant Effects of Low Dose of a Nuclease–Resistant Derivative of Polyinosinic Acid. Polycytidylic Acid on Antibody Responses of Monkeys to Inactivated Venezuelan Equine Encephalomyelitis Virus Vaccine," *Infect. Immun.* 24:160–166 (1979).
Hunter, R., et al., "Adjuvant Activity of Non–Ionic Block Copolymers. IV. Effect of Molecular Weight and Formulation of Titre and Isotype of Antibody," *Vaccine* 9:250–256 (1991).
Marx, P.A., et al., "Protection Against Vaginal SIV Transmission with Microencapsulated Vaccine," *Science* 28:1323–1327 (1993).
Mbawuike, I.N., et al., "Enhancement of the Protective Efficacy of Inactivated Influenza A Virus Vaccine in Aged Mice by IL–2 Liposomes," *Vaccine* 8:347–352 (1990).
Mowat, A.M., and Donachie, A.M., "ISCOM—A Novel Strategy for Mucosal Immunization?" *Immunol. Today* 12:383–385 (1991).
Newman, M.J., et al., "Saponin Adjuvant Induction of Ovalbumin–Specific CD8+ Cytotoxic T Lymphocyte Responses," *J. Immunol.* 148:2357–2362 (1992).
Phillips, N.C. and Emili, A., "Enhancement Antibody Response to Liposome–Associated Protein Antigens: Preferential Stimulation of IgG2a/b Production," *Vaccine* 10:151–158 (1992).
Relyveld, E.H., "Preparation and Use of Calcium Phosphate Adsorbed Vaccines," *Develop. Biol. Standard.* 65:131–136 (1986).

(List continued on next page.)

*Primary Examiner*—Mark Navarro
(74) *Attorney, Agent, or Firm*—Sterne, Kessler, Goldstein & Fox P.L.L.C.

(57) ABSTRACT

A vaccine containing one or more synthetic or highly purified natural peptides or proteins as antigen(s) as well as one or more adjuvants is present in the form of a solution or emulsion which is free from inorganic salt ions or has a low concentration of salt ions. Preferably, it contains substances capable of making the vaccine isotonic, particularly sorbitol.

28 Claims, 3 Drawing Sheets

OTHER PUBLICATIONS

Figure 1:
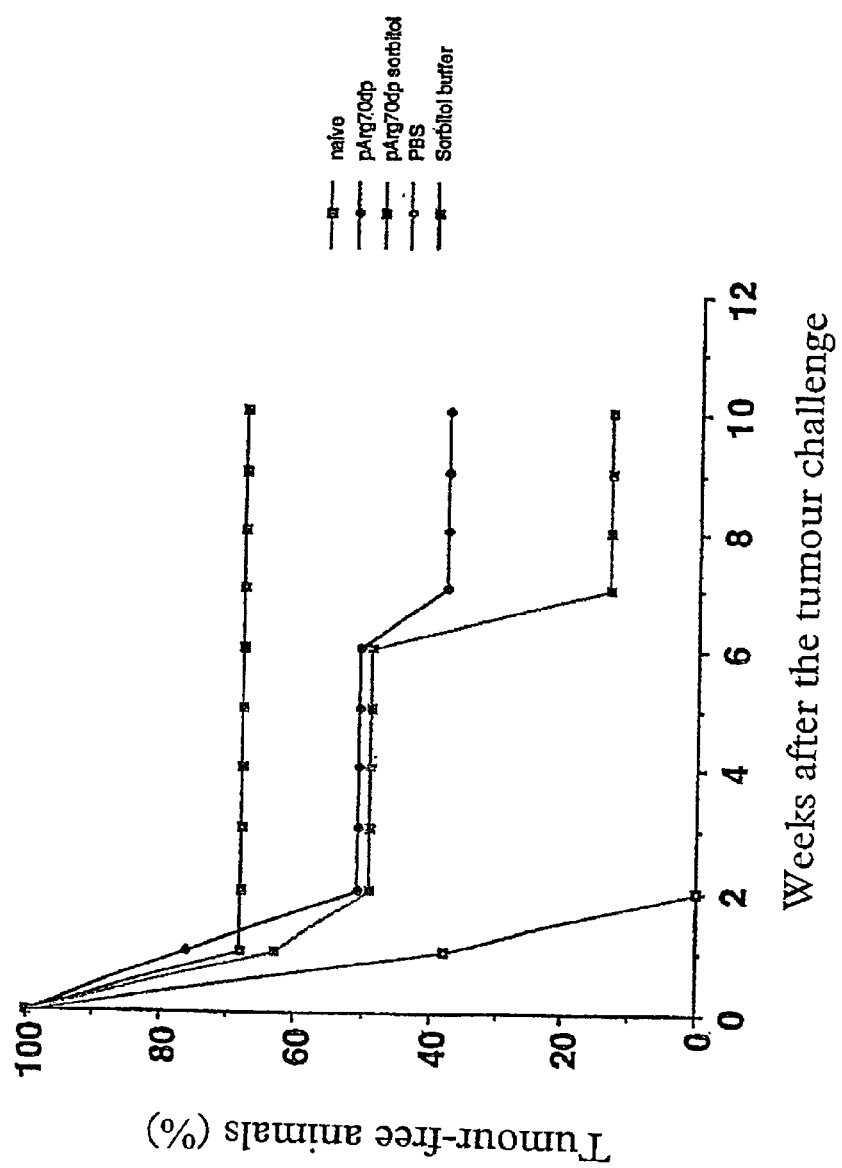

Ribi, E., "Beneficial Modification of the Endotoxin Molecule," *J. Biol. Response Modifiers* 3:1–9 (1984).

Stuart–Harris, C.H., "Adjuvant Influenza Vaccines," *Bulletin of the World health Org.* 41:617–621 (1969).

Takahashi, H., et al., "Induction of CD8+ Cytotoxic T Cells By Immunization with Purified HIV–1 Envelope Protein in ISCOMs," *Nature* 344:873–875 (1990).

Thaper, M.A., et al., "Secretory Immune Responses in the Mouse Vagina After Parenteral or Intravaginal Immunization with an Immunostimulating Complex (ISCOM)," *Vaccine* 9:129–133 (1991).

Vogel, F.R., "Immunologic Adjuvants for Modern Vaccine Formulations," *Ann. N.Y. Acad. Sci.* 754:153–160 (1995).

Warren, H.S., et al., "Current Status of Immunological Adjuvants," *Ann. Rev. Immunol.* 4:369–388 (1986).

Waters, R.V., et al., "Uveitis Induction in the Rabbit by Muramyl Dipeptides," *Infect. Immun.* 51:816–825 (1986).

* cited by examiner

SEQUENCE LISTING

```
<160> NUMBER OF SEQ ID NOS: 3

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: MHC Class I
      binding peptide

<400> SEQUENCE: 1

Ser Tyr Phe Pro Glu Thr His Ile
  1               5

<210> SEQ ID NO 2
<211> LENGTH: 9
<212> TYPE: PRT
<213> ORGANISM: Artificial Sequence
```

-continued

```
<220> FEATURE:
<223> OTHER INFORMATION: Description of Artificial Sequence:
      Fluorescence-labelled peptide

<400> SEQUENCE: 2

Leu Phe Glu Ala Ile Glu Gly Phe Ile
 1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:
      Fluorescence-labelled peptide

<400> SEQUENCE: 3

Gly Tyr Lys Asp Gly Asn Glu Tyr Ile
 1               5
```

VACCINE FORMULATIONS

The present invention relates to the field of vaccines.

The immunogenic effect of traditional vaccines is mostly based on pathogens which have been killed or attenuated. In traditional vaccines the impurities in the vaccines themselves or other components of organisms act as adjuvants which potentiate and/or prolong the immunogenic activity of the actual antigen. For example, the diphtheria-tetanus-whooping cough vaccine contains two potent adjuvants originating from the whole-cell whooping cough vaccine (LPS=lipopolysaccharide and PT=pertussis toxin); Similarly, the whole cell typhus and cholera vaccines have potent adjuvants (LPS and cholera toxin); the BCG vaccine (Bacillus Calmette Guerin) has powerful non-specific immunostimulatory effects.

In contrast to the complex traditional vaccines, modern vaccines contain synthetic, recombinant or highly purified antigens in the form of proteins or peptides. These vaccines are regarded as safer but generally have the disadvantage of lower immunogenicity. To compensate for this disadvantage, adjuvants are added to the vaccines, to increase and prolong the specific immune response to antigens. Some adjuvants have the property of intensifying T-cell proliferation and the cellular immune response.

Most of the adjuvants used hitherto have side effects, however, and furthermore these adjuvants do not meet the requirements imposed on the safety of adjuvants, such as stability with respect to adjuvant activity, minimal toxicity with no interaction with the antigen, and also degradability in the body and the absence of any immunogenic activity of their own.

A summary of current adjuvants which have hitherto been considered for use in vaccines is provided by Vogel, 1995, and by Gupta and Siber, 1995. They include: inorganic adjuvants in gel form (aluminium hydroxide/aluminium phosphate, calcium phosphate); bacterial adjuvants such as monophosphoryl lipid A and muramyl peptides, particulate adjuvants such as the so-called ISCOMS ("immunostimulatory complexes"), liposomes and biodegradable microspheres, adjuvants based on oil emulsions and emulsifiers such as Freund's adjuvant or IFA ("Incomplete Freund's adjuvant"), saponines (such as QS-21), squalene; synthetic adjuvants such as non-ionic block copolymers, muramyl peptide analogues, synthetic lipid A, synthetic polynucleotides and polycationic adjuvants such as polyarginine or polylysine (WO 97/30721).

The choice of an adjuvant is usually a compromise which is the result of balancing the toxicity and adjuvant effect of the substance in question.

In vaccine formulations, care has generally been taken up to now to achieve isotonicity; the common vaccine formulations are usually in a salt concentration which corresponds to about 150 mM of NaCl (about 300 mosmol/l). Common buffer formulations are PBS and HBS (phosphate-buffered or HEPES-buffered saline); e.g. for an ISCOM vaccine PBS pH 7.4 was proposed (Barr and Mitchell, 1996).

The aim of the present invention was to provide a vaccine formulation which intensifies the activity of vaccines based on antigens in the form of peptides or proteins.

It was found that, surprisingly, the immunogenic activity of a peptide-based vaccine containing adjuvant is increased if the vaccine formulation has a low concentration of salt ions or is free from salts.

The invention thus relates to a vaccine containing one or more synthetic or highly purified natural peptides or proteins as antigen(s) as well as one or more adjuvants. The vaccine is characterised in that it takes the form of a solution or emulsion which is free from inorganic salt ions or has a low concentration of salt ions.

In the context of the vaccine according to the invention the phrase "low concentration of salt ions" denotes a concentration which is equal to or less than about 50% of the salt concentration of an isotonic solution, corresponding to about 75 mM saline solution.

For calculating the ion concentration it should be borne in mind that, when using peptide or protein antigens which themselves have a charge, this charge is not taken into account.

Preferably, the vaccine is substantially free from sodium, chloride and phosphate ions, and particularly preferably it is substantially free from all inorganic salt ions ("substantially free" means that no salts have been added to the vaccine, but that there may be impurities present which have originated from reagents or there may be traces of ions; ions originating from adjuvants are not included in the calculation either, e.g. when using inorganic adjuvants).

In the event that the vaccine contains phosphate ions, e.g. originating from buffer solution, it is preferably free from sodium and chloride ions. If it contains sodium and/or chloride ions, it is preferably free from phosphate ions.

In one embodiment of the invention the vaccine contains antigen and adjuvant in salt-free medium, e.g. in distilled water.

In another preferred embodiment the vaccine according to the invention contains one or more water-soluble or water-emulsifiable substances which are capable of making the vaccine isotonic and increasing its immunogenic activity.

These substances are hereinafter designated "isotonic-making substances". Isotonic-making substances have the property of being able to generate physiological osmotic pressure by virtue of their molecular size and molecular structure.

Preferably, the isotonic-making substances are selected from among the group carbohydrates (sugars, sugar alcohols, oligosaccharides, polysaccharides), polyhydric alcohols, amino acids or lipids.

Preferably, the isotonic-making substance is a sugar, particularly a mono- or disaccharide such as maltose, fructose, galactose or saccharose, or a sugar alcohol such as sorbitol or mannitol.

The amino acids used may be isotonic, salt-free amino acid solutions such as are used e.g. in parenteral feeding. Solutions of this kind are commercially obtainable (e.g. from Leopold, Graz, Austria); if necessary they may be desalinated if they contain salt ions. Alternatively, isotonic, salt-free solutions which contain individual, preferably water-soluble, amino acids may be used.

The lipids used may be, in particular, isotonic, salt-free fatty emulsions such as those used in parenteral feeding, for example. Emulsions of this kind are commercially obtainable (e.g. from Leopold, Graz, Austria); if necessary they may be desalinated if they contain salt ions. It is also possible to use long-chain hydrocarbons (e.g. paraffin oils), and also higher fatty acids such as linoleic acid, linolenic acid or palmitic acid, and fatty acid esters such as triglycerides.

The isotonic-making substance is preferably present in a concentration such that the resulting solution is isotonic or slightly hypotonic, depending on the molecular weight.

Preferred sugar or sugar alcohol concentrations are within the range from about 200–400 mM, particularly in the range from 250–300 mM. The osmolarity of the solution is conveniently between 200–400 mosmol/l, but the solution may also be strongly hypotonic.

Amino acid solutions should preferably have an osmolarity of between 200–400 mosmol/l, but may also be strongly hypotonic.

Lipid emulsions also preferably have an osmolarity of between 200–400 mosmol/l, but may also be strongly hypotonic.

In addition to the isotonic-making substance the solution comprising the vaccine according to the invention optionally contains a buffer substance. This might be, in particular, HEPES (N-[2-hydroxyethyl]piperazine-N'-[2-ethanesulphonic acid]), or TRIS (tris[hydroxymethyl]aminomethane). A buffer substance may be necessary to adjust the vaccine to a physiological pH if the primary solution is different from the physiological value.

The vaccine according to the invention is not subject to any restrictions regarding the peptide or protein antigens. The antigens may be naturally occurring immunogenic proteins, e.g. proteins from viral or bacterial pathogens or the fragments thereof or cellular breakdown products in the form of peptides; or tumour antigens or fragments thereof. In a preferred embodiment the antigen is a tumour antigen or a natural or synthetic peptide derived therefrom; in this case the vaccine is a tumour vaccine.

The quantity of effective antigen in the vaccine according to the invention may vary over a wide range.

The quantity of peptide depends, among other things, on the method of administration and the particular formulation used. The amount of peptide to be administered may be about 0.1 μg to about 10000 μg per vaccination dose, generally 1.0 μg to about 1000 μg, particularly about 10 μg to about 500 μg.

In a preferred embodiment of the invention the adjuvant is a substance such as that proposed in WO 97/30721, the disclosure of which is expressly referred to here, as an additive for protein or peptide vaccines, preferably a polycation such as polyarginine or polylysine which is optionally modified, e.g. with a sugar group.

The adjuvant used may also be, theoretically, any of the abovementioned adjuvants known for peptide- or protein-based vaccines. For example: inorganic adjuvants in gel form (aluminium hydroxide/aluminium phosphate, Warren et al., 1986; calcium phosphate, Relyvelt, 1986); bacterial adjuvants such as monophosphoryl lipid A (Ribi, 1984; Baker et al., 1988) and muramyl peptides (Ellouz et al., 1974; Allison and Byars, 1991; Waters et al., 1986); particulate adjuvants such as the so-called ISCOMS ("immunostimulatory complexes", Mowat and Donachie, 1991; Takahashi et al., 1990; Thapar et al., 1991), liposomes (Mbawuike et al. 1990; Abraham, 1992; Phillips and Emili, 1992; Gregoriadis, 1990) and biodegradable microspheres (Marx et al., 1993); adjuvants based on oil emulsions and emulsifiers such as Freund's adjuvant or IFA ("Incomplete Freund's adjuvant" (Stuart-Harris, 1969; Warren et al., 1986), SAF (Allison and Byars, 1991), saponines (such as QS-21; Newman et al., 1992), squalene/squalane (Allison and Byars, 1991); synthetic adjuvants such as non-ionic block copolymers (Hunter et al., 1991), muramyl peptide analogues (Azuma, 1992), synthetic lipid A (Warren et al., 1986; Azuma, 1992), synthetic polynucleotides (Harrington et al., 1978) and polycationic adjuvants (WO 97/30721).

The skilled person will be able to define suitable antigen/adjuvant formulations from the specialist literature mentioned hereinbefore and, working from this starting point, find an isotonic-making substance which is capable of increasing the efficacy of the formulation or, while retaining the same efficacy, reducing the proportion of adjuvant in the formulation, which offers a critical advantage in the case of adjuvants with side effects.

It has surprisingly been found, within the scope of the present invention, that a salt-free tumour vaccine made isotonic with sorbitol, containing an MHC-binding peptide derived from a tumour antigen as well as polyarginine as adjuvant, has a more potent antitumour activity than a conventionally formulated tumour vaccine, i.e. containing an isotonic salt concentration, which is identical in terms of the peptide/adjuvant. It was found that the peptides together with the adjuvant dissolve better in sorbitol solution than in conventional PBS buffer. Without wishing to be tied to the theory, the improved activity of the vaccine, apart from the improved solubility, would appear to be due to the fact that the interaction between the peptide and adjuvant is made easier and thus the activity of the adjuvant is intensified. The improved activity of the vaccine may possibly also be due to a co-adjuvant activity of the isotonic-making substance, e.g. sorbitol, i.e. this substance (sorbitol) as such has a certain adjuvant effect which increases the activity of the primary adjuvant.

The following method is appropriately used to achieve the ideal vaccine formulation: starting from a defined antigen, which is intended to provoke the desired immune response, in a first step an adjuvant matched to the antigen is found, as described in the specialist literature, particularly in WO 97/30721. In a next step the vaccine is optimised by adding various isotonic-making substances as defined in the present inventions, preferably sugars and/or sugar alcohols, in an isotonic or slightly hypotonic concentration, to the mixture of antigen and adjuvant, with the composition otherwise being identical, and adjusting the solution to a physiological pH in the range from pH 4.0 to 10.0, particularly 7.4. Then, in a first step as described in the example of the present application, the substances or the concentration thereof which will improve the solubility of the antigen/adjuvant composition compared with a conventional, saline-buffered solution are determined. The improvement in the solubility characteristics by a candidate substance is a first indication that this substance is capable of bringing about an increase in the immunogenic activity of the vaccine.

Since one of the possible prerequisites for an increase in the cellular immune response is increased binding of the antigen to APCs (antigen presenting cells), in a next step an investigation can be made to see whether the substance leads to an increase of this kind. The procedure used may be analogous to that described in the definition of the adjuvant, e.g. incubating APCs with fluorescence-labelled peptide or protein, adjuvant and isotonic-making substance. An increased uptake or binding of the peptide to APCs brought about by the substance can be determined by comparison with cells which have been mixed with peptide and adjuvant alone or with a peptide/adjuvant composition which is present in conventional saline buffer solution, using throughflow cytometry.

In a second step the candidate substances may be investigated in vitro to see whether and to what extent their presence is able to increase the presentation of a peptide to APCs; the MHC concentration on the cells may be measured using the methods described in WO 97/30721 for testing peptides.

Another possible way of testing the efficiency of a formulation is by using an in vitro model system. In this, APCs are incubated together with adjuvant, peptide and candidate substance and the relative activation of a T-cell clone which specifically recognises the peptide used is measured (Coligan et al., 1991; Lopez et al., 1993).

The efficiency of the formulation may optionally also be demonstrated by the cellular immune response by detecting a "delayed-type hypersensitivity" (DTH) reaction in immunised animals.

Finally, the immunomodulatory activity of the formulation is measured in animal tests. In the case of a tumour vaccine as in the present example, established tumour models having known peptide sequences recognised by immune cells may be used, inter alia. The vaccine, containing different buffer substances but having a constant peptide/adjuvant composition, is administered to the test animals. The protection from tumour growth is a measurement of the efficacy of a tumour vaccine.

EXAMPLE

The experiments were carried out as described in WO 97/30721.

a) DBA/2 mice were inoculated three times at intervals of one week with a mixture of 100 μg of MHC Class I binding peptide SYFPETHI (SEQ ID NO: 1) (known as "P815 JAK1") and 75 μg of polyarginine (degree of polymerisation 70, SIGMA Chemicals, St. Louis Mo.) per animal. The peptide/adjuvant solution was administered in sorbitol solution (270 mM sorbitol, 5 mM HEPES) or phosphate-buffered saline solution (PBS, GIBCO BRL). Control mice were either given 100 μg of peptide/animal with no adjuvant in sorbitol buffer or were not vaccinated. A week after the last vaccination, 104 viable tumour cells were injected and tumour growth was measured weekly.

The results of the tests are shown in FIG. 1. The Figure shows a comparison of the efficiency of the P815 JAK1 vaccine in sorbitol solution as against a vaccine in buffered isotonic saline solution in the animal model. It was found that animals that had been given the vaccine in sorbitol solution were better protected than mice that had been inoculated with peptide/polyarginine in BS.

b) For the solubility tests, mixtures of fluorescence-labelled peptide LFEAIEGFI (SEQ ID NO:2) or GYKDGNEYI (SEQ ID NO:2) were prepared: 100 μg of fluorescence-labelled peptide were combined with 75 μg of polyarginine (Arg; degree of polymerisation 70, SIGMA Chemicals, St. Louis Mo.) either in sorbitol solution or HEPES-buffered saline solution (HBS: 20 mM HEPES pH 7.5, 150 mM NaCl). After three hours the amount of dissolved fluorescence was measured by determining the extinction at 490 nM. The test protein used was Green Fluorescent protein.

Figure 2:
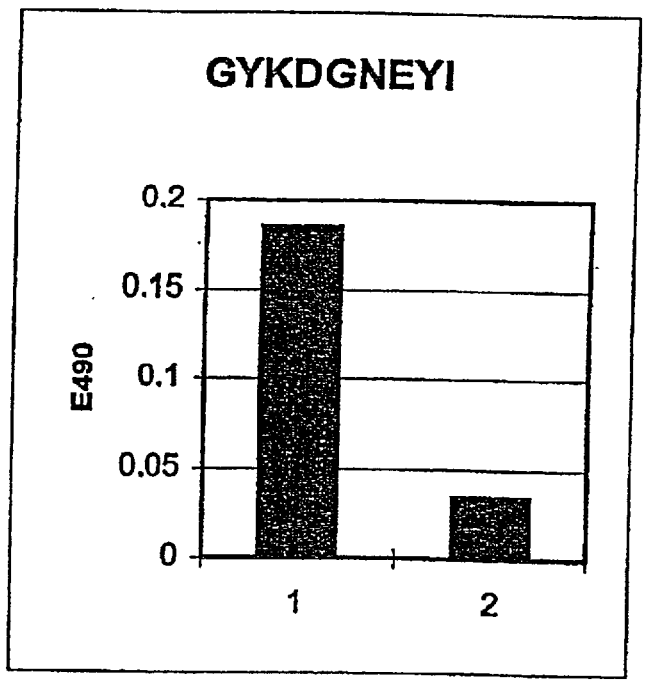
Figure 2:
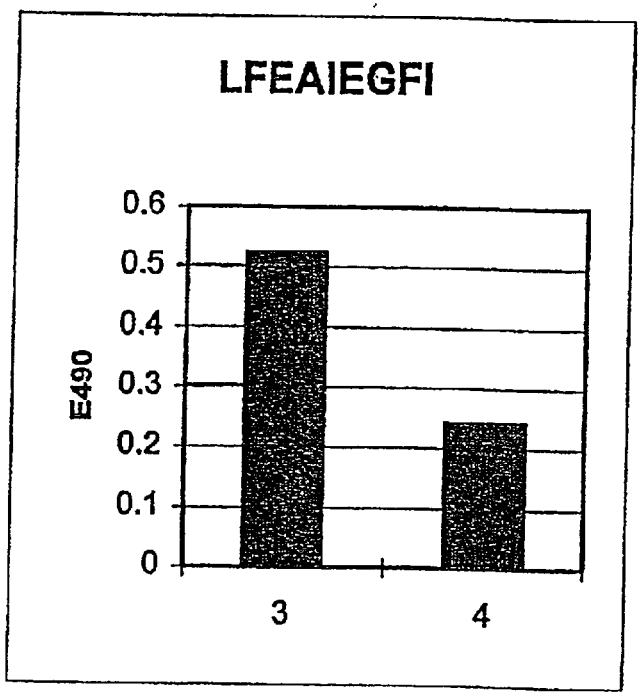
Figure 3:
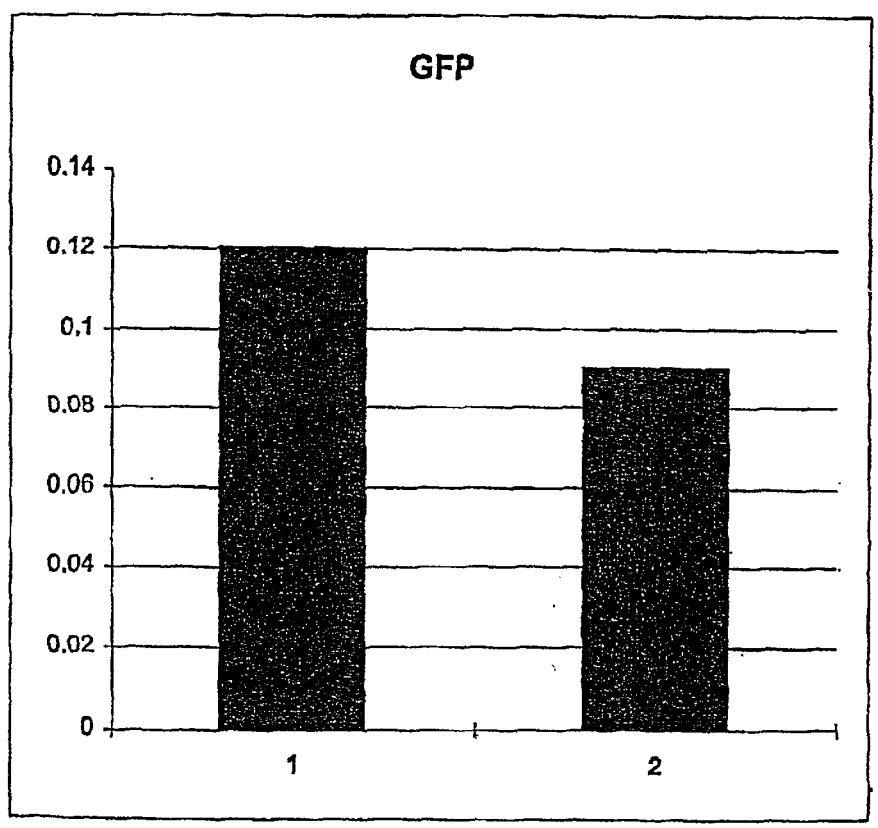

FIG. 2 and FIG. 3 show a comparison of the solubility of the complexes after mixing in buffered saline solution or sorbitol solution. The two fluorescence-labelled peptides (FIG. 2A and FIG. 2B) and the Green Fluorescent protein (GFP; about 30 Kd; FIG. 3) were included in this experiment. Adding the vaccine in sorbitol solution resulted in a significantly better solubility and recovery (increased fluorescence) both with the two tested peptides and with GFP.

LITERATURE

Abraham, E., 1992, Vaccine 10, 461–468
Allison, A. C., and Byars, N. E., 1991, Mol Immunol 28, 279–284
Azuma, I., 1992, Vaccine 10, 1000–1004
Baker, P. J., et al., 1988, Infect Immun 56, 3064–3066
Coligan, J. E. et al., 1991, Current Protocols in Immunology, Wiley, New York
Ellouz, F., et al., 1974, Biochem Biophys Res Commun 59, 1317–1325
Gupta, R. K. and Siber G. R., 1995, Vaccine 13, 1263–1276
Gregoriadis, G., 1990, Immunol Today 11, 89–97
Harrington, D. G., et al., 1978, Infect Immun 24, 160–166
Hunter, R., et al., 1991, Vaccine 9, 250–255
Lopez, J. A., et al., 1993, Eur. J. Immunol. 23, 217–223
Marx, P. A., et al., 1993, Science 28, 1323–1327
Mbawuike, I. N., et al., 1990, Vaccine 8, 347–352
Mowat, A. M., and Donachie, A. M., 1991, Immunol Today 12, 383–385
Newman, M. J., et al., 1992, J Immunol 148, 23572362
Phillips, N. C. and Emili, A, 1992, Vaccine 10, 151–158
Rammensee, H. G., et al., 1995, Immunogenetics 41, 178–228
Relyvelt, E. H., 1986, Develop Biol Standard, 65, 131–136
Ribi, E., 1984, J Biol Res Mod, 3, 1–9
Stuart-Harris, C. H., 1969, Bull WHO 41, 617–621
Takahashi, H., et al., 1990, Nature 344, 873–875
Thapar, M. A., et al., 1991, Vaccine 9, 129–133
Vogel, F. R. 1995, Ann N Y Acad Sci 754, 153–160
Warren, H. S., et al., 1986, Ann Rev Immunol 4, 369–388
Waters, R. V., et al., 1986, Infect Immun 52, 816–825

What is claimed is:

1. Vaccine containing one or more synthetic or purified natural peptides or proteins as antigen(s) as well as one or more adjuvants, characterised in that it is present as a solution or emulsion which is substantially free from inorganic salt ions, wherein said solution or emulsion contains one or more water soluble or water-emulsifiable substances which is capable of making the vaccine isotonic or hypotonic, said substance(s) selected from the group consisting of:
   a) a maltose;
   b) a fructose;
   c) a galactose;
   d) a saccharose;
   e) a sugar alcohol;
   f) a lipid; and
   g) combinations thereof,
wherein at least one of said adjuvants is a polycation, optionally modified with a sugar group.

2. Vaccine according to claim 1, characterized in that said water soluble or water-emulsifiable substance is present in a concentration such that the resulting solution is isotonic.

3. Vaccine according to claim 1, characterized in that it additionally contains a buffer.

4. Vaccine according to claim 1, characterized in that it contains a peptide as the antigen.

5. Vaccine according to claim 4, characterized in that the peptide is a tumour antigen or a fragment thereof and is capable of binding to MHC molecules.

6. Vaccine according to claim 1, characterized in that it contains polyarginine as the adjuvant.

7. Vaccine according to claim 1, characterized in that said water soluble or water-emulsifiable substance is present in a concentration such that the resulting solution is hypotonic.

8. The vaccine formulation of claim 1, wherein said water soluble or water-emulsifiable substance is a sugar alcohol.

9. The vaccine formulation of claim 1, wherein said water soluble or water-emulsifiable substance is maltose.

10. The vaccine formulation of claim 1, wherein said water soluble or water-emulsifiable substance is fructose.

11. The vaccine formulation of claim 1, wherein said water soluble or water-emulsifiable substance is galactose.

12. The vaccine formulation of claim 1, wherein said water soluble or water-emulsifiable substance is saccharose.

13. Vaccine according to claim 8, characterized in that the sugar alcohol is mannitol.

14. The vaccine formulation of claim 1, wherein said water soluble or water-emulsifiable substance is a lipid.

15. The vaccine formulation of claim 1, wherein said water soluble or water-emulsifiable substances are selected from the group consisting of maltose, fructose, galactose, saccharose and combinations thereof.

16. The vaccine formulation of claim 15, characterized in that the concentration of the water soluble or water-emulsifiable substances is in the range from about 200–400 mM.

17. The vaccine formulation of claim 16, characterized in that the concentration of the water soluble or water-emulsifiable substances is in the range from about 250–300 mM.

18. The vaccine formulation of claim 1, characterized in that the concentration of the water soluble or water-emulsifiable substances is in the range from about 200–400 mM.

19. The vaccine formulation of claim 18, characterized in that the concentration of the water soluble or water-emulsifiable substances is in the range from about 250–300 mM.

20. The vaccine according to claim 8, wherein said sugar alcohol is sorbitol.

21. The vaccine according to claim 8, characterized in that the concentration of sugar alcohol is in the range from about 200–400 mM.

22. The vaccine according to claim 20, characterized in that the concentration of sorbitol is 250–300 mM.

23. The vaccine according to claim 1, wherein said vaccine is in solution form.

24. The vaccine according to claim 1, wherein said vaccine is in emulsion form.

25. The vaccine according to claim 23, wherein said adjuvant is selected from the group consisting of polyarginine and polylysine.

26. The vaccine according to claim 25, wherein said adjuvant is polylysine.

27. The vaccine according to claim 26, wherein said isotonic making substance sugar alcohol.

28. The vaccine according to claim 27, wherein said sugar alcohol is sorbitol.

* * * * *